United States Patent [19]

Modena et al.

[11] Patent Number: 5,025,105
[45] Date of Patent: Jun. 18, 1991

[54] PROCESS FOR PREPARING BROMODIFLUOROACETYLFLUORIDE

[75] Inventors: Silvana Modena, Monza; Ezio Strepparola, Treviglio, both of Italy

[73] Assignee: AUSIMONT S.r.l., Milan, Italy

[21] Appl. No.: 544,581

[22] Filed: Jun. 27, 1990

[30] Foreign Application Priority Data

Jun. 28, 1989 [IT]   Italy ................................ 21016 A/89

[51] Int. Cl.$^5$ ............................................. C07C 51/58
[52] U.S. Cl. ................................................... 562/851
[58] Field of Search ........................................... 562/851

[56] References Cited

FOREIGN PATENT DOCUMENTS

| | | |
|---|---|---|
| 259818 | 3/1988 | European Pat. Off. . |
| 263309 | 4/1988 | European Pat. Off. . |
| 265052 | 4/1988 | European Pat. Off. . |
| 3707367 | 9/1988 | Fed. Rep. of Germany . |
| 79555 | 5/1983 | France . |
| 040435 | 3/1982 | Japan . |
| 045133 | 3/1982 | Japan . |
| 2082570 | 3/1982 | United Kingdom . |

OTHER PUBLICATIONS

Schaers, Carl et al., Inorg. Chem. 12(4) 897–900 1973.
Vogl, O. et al. ACS Symp. Ser. 59(Ring Opening Polym. 111–26, 1977.
Campbell, R. et al., Macro Mol. Chem. 180(3) 633–45, 1979.
Samejima, S. et al., Asahi Garash Kenkyo Hakoko 35(2) 165–73 1985.
Fukin, A. V., Tzv Akad. Nank SSSR Ser. Khim (7) 1572–6, 1984.
Chemical Abstracts, vol. 92, 41361 m, 1989.
Derwent Abstract of Japanese Patent Application 51/059818.

*Primary Examiner*—Paul J. Killos
*Attorney, Agent, or Firm*—Stevens, Davis, Miller & Mosher

[57] ABSTRACT

A process for preparing bromodifluoroacetylfluoride characterized in that a gaseous stream of oxygen-diluted ozone is reacted, at temperatures ranging from $-100°$ C. to $+80°$ C., with 1,4-dibromohexafluorobutene-2 optionally dissolved in a solvent which is inert under the reaction conditions, with consequent obtainment of the corresponding ozonide and, subsequently, the ozonide is subjected to a heat treatment at temperatures ranging from 100° to 300° C., with consequent obtainment of bromodifluoroacetylfluoride.

9 Claims, No Drawings

PROCESS FOR PREPARING BROMODIFLUOROACETYLFLUORIDE

DESCRIPTION OF THE INVENTION

The present invention relates to a process for preparing bromodifluoroacetylfluoride $CF_2Br-COF$.

Bromodifluoroacetylfluoride is a useful intermediate for the preparation of various fluoro-compounds. In particular it can be converted into omega-bromo-perfluorovinylethers, for example through the following reactions:

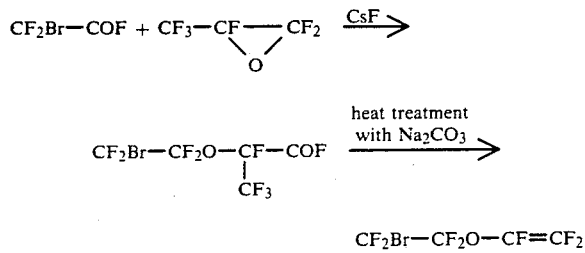

$$CF_2Br-CF_2O-CF=CF_2$$

In turn, the omega-bromo-perfluorovinylethers can be used as monomers for the copolymerization with fluorinated olefins: in this manner it is possible to obtain elastomers capable of cross-linking, by radical route.

According to British patent application No. 2,087,380, $CF_2Br-COF$ is prepared by treating $CF_2=CFX$ (wherein X is F, Cl, Br of I) with $Br_2$ and $SO_3$ and by heating the resulting intermediate product in fuming $H_2SO_4$ or in KF and sulpholane. This process provides a restricted selectivity.

According to the article by C. J. Schack, D. Pilipovich and J. F. Hon in Inorganic Chemistry, vol. 12, No. 4, 1973, 897-900, $CF_2Br-COF$ is prepared by reacting $CF_2=CFX$ (wherein X is F or Cl) with $BrOClO_3$ and by heating the resulting bromoperfluoroperchlorate with CsF or KF. This process is affected by low yields.

Thus, it is an object of the present invention to provide a process for preparing $CF_2Br-COF$ allowing to avoid the drawbacks of the abovesaid methods and which provides, by working according to particular conditions, practically quantitative yields of $CF_2Br-COF$.

This object and still further objects are achieved by the process of the present invention for preparing bromodifluoroacetylfluoride. This process is characterized in that a gaseous stream of oxygen-diluted ozone is reacted, at temperatures ranging from $-100°$ to $+80°$ C., with 1,4-dibromohexafluorobutene-2: $CF_2Br-CF=CF-CF_2Br$ optionally dissolved in a solvent which s inert under the reaction conditions, with consequent obtainment of the corresponding ozonide and, subsequently, the ozonide is subjected to a heat treatment, at temperatures ranging from 100° to 300° C., with consequent obtainment of bromodifluoroacetylfluroide.

The global first reaction step is as follows:

$$CF_2Br-CF=CF-CF_2Br + O_3 \longrightarrow \quad (1)$$

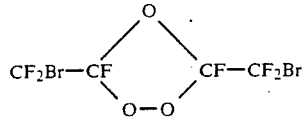

The second step reaction is as follows:

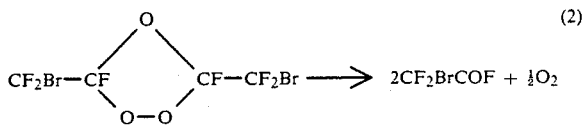

Preferably, a temperature ranging from $-80°$ to $+40°$ C. is employed in the first step, and a temperature ranging from 150° to 250° C., in the second step.

The oxygen and ozone mixture usually contains from 0.01 to 10% by volume of $O_3$; preferably, it contains from 1 to 6% by volume thereof.

The two reaction steps are usually conducted at atmospheric pressure. However it is also possible to operate, in the first and/or second step, at a pressure which is higher or lower than the atmospheric pressure.

According to a first embodiment of the invention, the first step is conducted without solvent or with a solvent of a first class which is liquid under the temperature and pressure conditions used in the first step and is gaseous under the temperature and pressure conditions used in the second step, and, on conclusion of the first step, the reaction mixture is transferred to a packed column, wherein the second step takes place. The packing material shall have a wide surface area (usually of at least 60 $m^2/g$), it must be stable under the temperature conditions of the second step and must be inert, under said temperature conditions, towards bromodifluoroacetylfluoride.

Suitable packing materials are, for example, activated carbon, styrene-divinylbenzene resins, zeolites and oxides of elements included in Group III A and IV A of Periodic Table. Preferably activated carbon or styrene-divinylbenzene resins are used.

Generally, the packing material surface area does not exceed 1,000 $m^2/g$ and materials having a surface area ranging from about 300 to about 500 $m^2/g$ are often preferred.

Among the solvents of the abovesaid first class, the following can be cited, by way of example:
(i) chlorofluorocarbons such as $CFCl_3$, $CF_2Cl-CFCl_2$ and the isomer mixtures of $C_3F_7Cl_3$ and $C_4F_6Cl_4$,
(ii) perfluoroalkanes having 6 to 9 carbon atoms,
(iii) perfluoropolyethers having a pour point lower than the temperature utilized in the first step. Examples of said compounds are perfluorodiglyme, perfluorotetraglyme and perfluoropolyether Galden ® D01 produced by Montefluos.

This first mode of embodiment is preferred because is secures practically quantitative $CF_2Br-COF$ yields. In accordance with a second mode of embodiment of the invention, the first step is conducted without solvent or with a solvent of the aforesaid first class or with a solvent of a second class which is liquid both under the temperature and pressure conditions of the firt step and under the ones of the second step, while the second step is conducted in the absence of packing material with the same reaction mixture of the first step or, when a solvent of the first class has been used in the first step, by substituting such solvent with a solvent of the second class.

More precisely, in accordance with the second mode of embodiment, when a solvent of the first class is used in the first step, it is possible to go on using it in the second step (wherein it passes to the gaseous state), or it can be substituted by a solvent of the second class before proceeding to the second step.

For replacing the solvent, it is possible to operate for example as follows: the solvent of the second class is added to the solution of the first step, whereafter the solvent of the first class is removed by distillation.

Suitable solvents of the second class are, for example, the chlorotrifluoroethylene telomers having a telomerization degree from 3 to 6 and the perfluoropolyethers having a boiling temperature higher than the temperature used in the second step and a pour point lower than the temperature employed in the first step. Among the suitable perfluoropolyethers, for example, the following commercial products can be cited: Galden ®, which have a kinematic viscosity at 20° C. higher than 2 cSt, Fomblin ® Y and Fomblin ®Z, all being produced by Montefluos.

When a solvent is used in the first step, the $O_3/O_2$ stream is made to flow into the liquid phase consisting of 1,4-dibromohexafluorobutene-2 and of its solvent till reaching, preferably, the complete conversion of the olefin. It is also possible to use a slight $O_3/O_2$ excess with respect to the stoichiometry of reaction (1), but, for safety reasons, it is advisable that the $O_3$ excess should not exceed 5% by moles with respect to tthe stoichiometric ratio with the olefin. Conversely, it is possible to stop the $O_3/O_2$ flow when the olefin conversion is partial: in this case it is generally operated in such manner as to obtain at least a 10% conversion.

When no solvent is used in the first step, it is advisable, for safety reasons, to stop the $O_3/O_2$ flow before the olefin conversion exceeds 50%.

When the second step is carried out in a packed column, it is possible to convey to the column, along with the reaction mixture, also an inert gas flow, for example a nitrogen or helium flow. Usually, the volume ratio between inert gas flow and ozonide flow ranges from 2:1 to 4:1.

The ozonide decomposition can be carried out in the presence of an aprotic reducing agent.

Among the suitable aprotic reducing agents it is possible to cite, for example, the following:

(a) fluorinated olefins, in particular the ones containing 2 to 4 carbon atoms;
(b) organic sulphides, for example dimethylsulphide;
(c) phosphines, for example triphenylphosphine.

The 1,4-dibromohexafluorobutene-2 concentration in its solvent, if any, can be varied over a wide range. Generally, a concentration ranging from 0.5 to 70% by volume and, preferably, from 5 to 40% is used.

When in the second step the solvent is substituted, the ozonide concentration is maintained unaltered.

When a reducing agent is utilized in the second step, it is used in an at least stoichiometric ratio with respect to the oxygen atom which gets free in reaction (2).

On conclusion of the second step, if a solvent of the first class has been used, $CF_2Br-COF$ is purified by means of knonw methods, for example by distillation, after condensation of the gaseous mixture; if a solvent of the second class has been used, $CF_2Br-COF$ practically condenses already in the pure state.

EXAMPLES

The following examples are given merely for illustrative purposes and are not to be considered as a limitation of the present invention.

EXAMPLE 1

25 g (0.078 moles) of $CF_2Br-CF=CF-CF_2Br$ and 50 ml of $CFCl_3$ were charged into a cylindrical 100 cm$^3$ reactor made of AISI steel, equipped with a stand dipping pipe for the gas feeding and with a vent to the atmosphere for the outlet of said gases. After cooling to $-80°$ C., a gaseous stream of $O_2$ and $O_3$ at 4% by volume of $O_3$ was made to pass at a flowrate of 10N l/h for 4.5 hours.

A nitrogen stream was then fed for 30 minutes to remove the unreacted ozone which had remained dissolved in the solution. The solution was allowed to return at room temperature, then it was dropped at a rate of 20 g/h, under a nitrogen flow of 4N l/h, into a steel pipe heated to 150° C. and filled with styrene-divinylbenzene resin Amberlite ® XAD-2, produced by Rohm and Hass, having a surface area of 330 m$^2$/g. The pipe had an inside diameter of 4 mm and a length of 1 mm.

The gaseous products leaving the pipe were condensed at $-80°$ C. 27 g of $CF_2Br-COF$ (0.15 moles) were obtained in admixture with its solvent, from which it was distillable off.

EXAMPLE 2

It was operated as in example 1, except for the following modalities:
it was operated without solvent,
the $O_2$ and $O_3$ flow was made to pass for 2 hours.

The gaseous products condensed on conclusion of the second step consisted of 12.6 g of $CF_2Br-COF$ (0.071 moles) and of 13.5 g of unreacted $CF_2Br-CF=CF-CF_2Br$ (0.042 moles).

EXAMPLE 3

In the first step it was operated as in example 1, except that the $O_3/O_2$ stream was made to pass at a flowrate of 20N l/h for 4 hours.

A nitrogen flow was then fed for 1 hour in order to remove the unreacted ozone which remained dissolved in the solution. The solution was allowed to return at room temperature and then it was heated to 150° C. for 4 hours. On conclusion of the reaction, the gaseous products leaving the reactor were condensed at $-80°$ C. About 17 g of $CF_2BrCOF$ (about 0.096 moles) in admixture with its solvent were obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A process for preparing bromodifluoroacetylfluoride, comprising a gaseous stream of oxygen-diluted ozone is reacted, at a temperature ranging from $-100°$ to $+80°$ C., with 1,4-dibromohexafluorobutene-2, optionally dissolved in a solvent which is inert under the reaction conditions, with consequent obtainment of the corresponding ozonide and, subsequently, the ozonide is subjected to a heat treatment, at temperatures ranging from 100° to 300° C., with consequent obtainment of bromodifluoroacetylfluroide.

2. The process according to claim 1, comprising the reaction between ozone and 1,4-dibromohexafluorobutene-2 is conducted at a temperature ranging from −80° to +40° C.

3. The process according to claim 1, wherein the ozonide is heat-treated at a temperature ranging from 150° to 250° C.

4. The process according to claim 1, wherein the gaseous stream of oxygen-diluted ozone contains from 0.01 to 10% by volume of ozone.

5. The process according to claim 1, wherein the reaction step between ozone and 1,4-dibromohexafluorobutene-2 (first step) either no solvent is used or use is made of a solvent of a first class which is liquid under the temperature and pressure conditions employed in the first step and is gaseous under the temperature and pressure conditions employed in the ozonide heat treatment step (second step), and that, at the end of the first step, the reaction mixture is transferred into a packed column packed wit a material which exhibits a great surface area, is stable under the temperature conditions of the second step and is inert, under said temperature conditions, towards bromodifluoroacetylfluoride.

6. The process according to claim 5, wherein the packing material is selected from the group consisting of activated carbon, styrene-divinylbenzene resins, zeolites and oxides of elements included in Groups III A and IV A of Periodic Table of Elements.

7. The process according to claim 1, wherein the first step is conducted without solvent or with a solvent of the aforesaid first class, or with a solvent of a second class which is liquid both under the temperature and pressure conditions of the first step and under the ones of the second step, and that the second step is conducted in the absence of packing material with the same reaction mixture of the first step, or, when a solvent of the first class has been used in the first step, by substituting said solvent with a solvent of the second class.

8. The process according to claim 1, wherein the solvent of the first class is selected from the group consisting of chlorofluorocarbons, perfluoroalkanes having 6 to 9 carbon atoms and perfluoropolyethers having a pour point lower than the temperature used in the first step.

9. The process according to claim 1, herein the solvent of the second class is selected from the group consisting of clhorotrifluoroethylene telomers having a telomerization degree from 3 to 6 and of perfluoropolyethers having a boiling temperature higher than the temperature used in the second step and a pour point lower than the temperature employed in the first step.

* * * * *